United States Patent
Khamene et al.

(10) Patent No.: US 7,570,738 B2
(45) Date of Patent: Aug. 4, 2009

(54) FOUR-DIMENSIONAL (4D) IMAGE VERIFICATION IN RESPIRATORY GATED RADIATION THERAPY

(75) Inventors: Ali Khamene, Princeton, NJ (US);
Charles Henri Florin, Exton, PA (US);
Juan Carlos Celi, Bensheim (DE);
Barbara Ofstad, Weinheim (DE);
Mikael Rousson, Trenton, NJ (US);
Frank Sauer, Princeton, NJ (US);
Christian Schaller, Teublitz (DE)

(73) Assignees: Siemens Medical Solutions USA, Inc., Malvern, PA (US); Siemens Aktiengesellschaft, München (DE)

( * ) Notice: Subject to any disclaimer, the term of this patent is extended or adjusted under 35 U.S.C. 154(b) by 174 days.

(21) Appl. No.: 11/831,090

(22) Filed: Jul. 31, 2007

(65) Prior Publication Data
US 2008/0031404 A1 Feb. 7, 2008

Related U.S. Application Data

(60) Provisional application No. 60/835,528, filed on Aug. 4, 2006.

(51) Int. Cl.
*A61N 5/10* (2006.01)
*A61B 6/02* (2006.01)
*A61B 6/03* (2006.01)

(52) U.S. Cl. .............................. 378/65; 378/8; 378/20; 378/41; 378/42; 378/95; 600/428

(58) Field of Classification Search .................... 378/8, 378/20, 41, 42, 65, 95; 600/428
See application file for complete search history.

(56) References Cited

U.S. PATENT DOCUMENTS

| | | | |
|---|---|---|---|
| 6,865,253 B2 * | 3/2005 | Blumhofer et al. | 378/65 |
| 6,889,695 B2 * | 5/2005 | Pankratov et al. | 128/898 |
| 7,010,080 B2 * | 3/2006 | Mitschke et al. | 378/8 |
| 7,158,610 B2 * | 1/2007 | Mostafavi | 378/98.12 |
| 7,260,426 B2 * | 8/2007 | Schweikard et al. | 600/407 |
| 2004/0092815 A1 | 5/2004 | Schweikard et al. | |
| 2005/0053196 A1 | 3/2005 | Mostafavi | |
| 2005/0180544 A1 | 8/2005 | Sauer et al. | |
| 2006/0074292 A1 | 4/2006 | Thomson et al. | |

* cited by examiner

*Primary Examiner*—Allen C. Ho
(74) *Attorney, Agent, or Firm*—Donald B. Paschburg; F. Chau & Associates, LLC (57) ABSTRACT

A method for four-dimensional (4D) image verification in respiratory gated radiation therapy, includes: acquiring 4D computed tomography (CT) images, each of the 4D CT images representing a breathing phase of a patient and tagged with a corresponding time point of a first surrogate signal; acquiring fluoroscopic images of the patient under free breathing, each of the fluoroscopic images tagged with a corresponding time point of a second surrogate signal; generating digitally reconstructed radiographs (DRRs) for each breathing phase represented by the 4D CT images; generating a similarity matrix to assess a degree of resemblance in a region of interest between the DRRs and the fluoroscopic images; computing a compounded similarity matrix by averaging values of the similarity matrix across different time points of the breathing phase during a breathing period of the patient; determining an optimal time point synchronization between the DRRs and the fluoroscopic images by using the compounded similarity matrix; and acquiring a third surrogate signal and turning a treatment beam on or off according to the optimal time point synchronization.

28 Claims, 5 Drawing Sheets

FOUR-DIMENSIONAL (4D) IMAGE VERIFICATION IN RESPIRATORY GATED RADIATION THERAPY

CROSS-REFERENCE TO RELATED APPLICATION

This application claims the benefit of U.S. Provisional Application No. 60/835,528, filed Aug. 4, 2006, the disclosure of which is incorporated by reference herein in its entirety.

BACKGROUND OF THE INVENTION

1. Technical Field

The present invention relates to four-dimensional (4D) image verification in respiratory gated radiation therapy.

2. Discussion of the Related Art

Radiation therapy is a treatment modality with the primary goal of precisely delivering a prescribed dose of radiation to a tumor while minimizing an amount of the dose delivered to surrounding healthy tissues and critical structures. Recent technological advances in radiation therapy have enabled the delivery of a highly conformal radiation dose distribution to a morphologically complex target volume. Notwithstanding these recent advances, miss-delivery of the dose can occur because of inter-fraction and intra-fraction target motions.

Intra-fraction target motion, e.g., movement of the host organ, is generally caused by patient respiration. Respiration induced tumor motion has been studied indirectly by analyzing movements of the host organ using radio-opaque markers (implanted near the tumor or in a surrogate organ/structure). Real-time imaging technologies have been used to observe tumor motion or indirectly perceive tumor motion. Using such technologies it has been shown that tumor motion can be as large as, e.g., 2-6 cm. The variation in the size of the motion as well as the pattern of the motion can make the identification of the location of a tumor difficult.

There are three general approaches to dealing with tumor motion in radiation treatment. In the first method, which is clinically used, a patient is told to hold their breath or to do forced shallow breathing. A drawback of this method is that it requires patient compliance. In the second and third methods, a patient can exercise free breathing. In the second method, which is referred to as "gating", a radiation beam is gated in a way such that the tumor is only treated at a prescribed or planned position. In the third method, which is referred to as "tracking", a radiation beam or a treatment table is moved so that the tumor always remains at a fixed point within the treatment field.

Respiratory gating of the radiation beam is limited to a fraction of the patient's breathing cycle, during which the tumor is in the treatment field. In the tracking technique, the radiation beam follows the target dynamically throughout the entire breathing cycle. It is technically challenging to implement linear accelerator (LINAC)-based tracking using a dynamic multi-leaf collimator mainly due to quality assurance issues. In contrast, respiratory gating is more practical, and has been adopted in clinical practice by a number of cancer centers. However, a challenge of respiratory gated treatment is to adapt the gating intervals based on current breathing patterns of the patient.

Respiratory gated radiation therapy generally involves two approaches. In the first approach, an internal surrogate organ is used to detect tumor motion. Here, a real-time imaging system, such as an X-ray in fluoroscopic mode, provides position information of implemented markers at the tumor site that are indicative of the tumor motion. In the second approach, an external surrogate is used. Here, various external surrogates such as a strain gauge taped on a patient's abdomen or back, retro-reflective optical markers, or airbags have been used.

One advantage of the external gating systems is that they are non-invasive. However, having an external signal is not equivalent to knowing the location of the tumor at all times. In addition, exploiting the external signal blindly can cause significant errors. In particular, the correlation between tumor motion and the surrogate signal may change over time. Thus, a drawback of this method is the variability of the correlation between the amplitude of the external signal (e.g., marker position) and the position of the internal target (e.g., tumor).

SUMMARY OF THE INVENTION

In an exemplary embodiment of the present invention, a method for four-dimensional (4D) image verification in respiratory gated radiation therapy, comprises: acquiring 4D computed tomography (CT) images, each of the 4D CT images representing a breathing phase of a patient and tagged with a corresponding time point of a first surrogate signal; acquiring fluoroscopic images of the patient under free breathing, each of the fluoroscopic images tagged with a corresponding time point of a second surrogate signal; generating digitally reconstructed radiographs (DRRs) for each breathing phase represented by the 4D CT images; generating a similarity matrix to assess a degree of resemblance in a region of interest between the DRRs and the fluoroscopic images; computing a compounded similarity matrix by averaging values of the similarity matrix across different time points of the breathing phase during a breathing period of the patient; determining an optimal time point synchronization between the DRRs and the fluoroscopic images by using the compounded similarity matrix; and acquiring a third surrogate signal and turning a treatment beam on or off according to the optimal time point synchronization.

Determining an optimal time point synchronization between the DRRs and the fluoroscopic images comprises drawing a path across the compounded similarity matrix for each DRR that is associated to a fluoroscopic image, wherein a path that links duplets of maximal similarity represents the optimal time point synchronization.

Determining an optimal time point synchronization between the DRRs and the fluoroscopic images comprises: building a cost matrix upon the compounded similarity matrix; building a position lookup table that contains values in the cost matrix; performing a backtracking using the position lookup table and the cost matrix to determine costs for paths in the cost matrix; and selecting a path with a lowest cost that represents the optimal time point synchronization.

Determining an optimal time point synchronization between the DRRs and the fluoroscopic images comprises: establishing a correspondence map between the DRRs and the fluoroscopic images; and minimizing an energy function to find an optimal mapping between the DRRs and the fluoroscopic images, the optimal mapping representing the optimal time point synchronization.

The energy function is a two term energy function, the first term evaluating a cost of similarity between the DRRs and the fluoroscopic images on the correspondence map and the second term evaluating a likelihood of a hypothesized fluoroscopic image sequence based on a learned Hidden Markov Model (HMM).

The method further comprises determining a consistency between the time points of the second surrogate signal and the time points of the third surrogate signal by using an Auto-Regressive (AR) model built according to the second surrogate signal.

The breathing period of the patient is an average breathing period that is determined by: generating an auto-similarity matrix and from this matrix selecting a row with a highest cumulated dissimilarity to generate a one-dimensional (1D) periodic signal; processing the 1D periodic signal to determine a best fitting AR model, the AR model built according to the second surrogate signal; and computing the average breathing period using the best fitting AR model.

The similarity matrix generated to assess a degree of resemblance in a region of interest between the DRRs and the fluoroscopic images is one or a combination of mutual information, correlation ratio, gradient correlation, gradient difference, normalized cross correlation or local normalized cross correlation.

After acquiring the 4D CT images and before acquiring the fluoroscopic images the method further comprises extracting a target volume from each of the 4D CT images and combining the target volumes to determine a gross target volume.

The region of interest is manually specified by a user or estimated from a position of the gross target volume on the DRRs and the fluoroscopic images. The first, second and third surrogate signals correspond to a target inside the patient. The target is a tumor location or a suspected location of a tumor.

In an exemplary embodiment of the present invention, a method for 4D image verification in respiratory gated radiation therapy, comprises: acquiring 4D CT images, each of the 4D CT images representing a breathing phase of a patient and tagged with a corresponding time point of a first surrogate signal; acquiring fluoroscopic images of the patient under free breathing, each of the fluoroscopic images tagged with a corresponding time point of a second surrogate signal; generating DRRs for each breathing phase represented by the 4D CT images; generating a similarity matrix to assess a degree of resemblance in a region of interest between the DRRs and the fluoroscopic images; determining an optimal time point synchronization between the DRRs and the fluoroscopic images during a breathing period of the patient by using the similarity matrix; and acquiring a third surrogate signal and turning a treatment beam on or off according to the optimal time point synchronization.

Determining an optimal time point synchronization between the DRRs and the fluoroscopic images comprises drawing a path across the similarity matrix for each DRR that is associated to a fluoroscopic image, wherein a path that links duplets of maximal similarity represents the optimal time point synchronization.

Determining an optimal time point synchronization between the DRRs and the fluoroscopic images comprises: building a cost matrix upon the similarity matrix; building a position lookup table that contains values in the cost matrix; performing a backtracking using the position lookup table and the cost matrix to determine costs for paths in the cost matrix; and selecting a path with a lowest cost that represents the optimal time point synchronization.

Determining an optimal time point synchronization between the DRRs and the fluoroscopic images comprises: establishing a correspondence map between the DRRs and the fluoroscopic images; and minimizing an energy function to find an optimal mapping between the DRRs and the fluoroscopic images, the optimal mapping representing the optimal time point synchronization.

The energy function is a two term energy function, the first term evaluating a cost of similarity between the DRRs and the fluoroscopic images on the correspondence map and the second term evaluating a likelihood of a hypothesized fluoroscopic image sequence based on a learned HMM.

The method further comprises determining a consistency between the time points of the second surrogate signal and the time points of the third surrogate signal by using an AR model built according to the second surrogate signal.

The breathing period of the patient is an average breathing period that is determined by: generating an auto-similarity matrix and from this matrix selecting a row with a highest cumulated dissimilarity to generate a 1D periodic signal; processing the 1D periodic signal to determine a best fitting AR model, the AR model built according to the second surrogate signal; and computing the average breathing period using the best fitting AR model.

The similarity matrix generated to assess a degree of resemblance in a region of interest between the DRRs and the fluoroscopic images is one of a combination of mutual information, correlation ratio, gradient correlation, gradient difference, normalized cross correlation or local normalized cross correlation.

After acquiring the 4D CT images and before acquiring the fluoroscopic images the method further comprises extracting a target volume from each of the 4D CT images and combining the target volumes to determine a gross target volume.

The region of interest is manually specified by a user or estimated from a position of the gross target volume on the DRRs and the fluoroscopic images. The first, second and third surrogate signals correspond to a target inside the patient. The target is a tumor location or a suspected location of a tumor.

In an exemplary embodiment of the present invention, a system for 4D image verification in respiratory gated radiation therapy, comprises: a memory device for storing a program; a processor in communication with the memory device, the processor operative with the program to: acquire 4D CT images, each of the 4D CT images representing a breathing phase of a patient and tagged with a corresponding time point of a first surrogate signal; acquire fluoroscopic images of the patient under free breathing, each of the fluoroscopic images tagged with a corresponding time point of a second surrogate signal; generate DRRs for each breathing phase represented by the 4D CT images; generate a similarity matrix to assess a degree of resemblance in a region of interest between the DRRs and the fluoroscopic images; compute a compounded similarity matrix by averaging values of the similarity matrix across different time points of the breathing phase during a breathing period of the patient; determine an optimal time point synchronization between the DRRs and the fluoroscopic images by using the compounded similarity matrix; and acquire a third surrogate signal and turn a treatment beam on or off according to the optimal time point synchronization.

In an exemplary embodiment of the present invention, a system for 4D image verification in respiratory gated radiation therapy, comprises: a memory device for storing a program; a processor in communication with the memory device, the processor operative with the program to: acquire 4D CT images, each of the 4D CT images representing a breathing phase of a patient and tagged with a corresponding time point of a first surrogate signal; acquire fluoroscopic images of the patient under free breathing, each of the fluoroscopic images tagged with a corresponding time point of a second surrogate signal; generate DRRs for each breathing phase represented by the 4D CT images; generate a similarity matrix to assess a degree of resemblance in a region of interest between the DRRs and the fluoroscopic images; determine an optimal time point synchronization between the DRRs and the fluoroscopic images during a breathing period of the patient by using the similarity matrix; and acquire a third surrogate signal and turn a treatment beam on or off according to the optimal time point synchronization.

In an exemplary embodiment of the present invention, a computer program product comprising a computer useable medium having computer program logic recorded thereon for 4D image verification in respiratory gated radiation therapy, the computer program logic comprises: program code for acquiring 4D CT images, each of the 4D CT images representing a breathing phase of a patient and tagged with a corresponding time point of a first surrogate signal; program code for acquiring fluoroscopic images of the patient under free breathing, each of the fluoroscopic images tagged with a corresponding time point of a second surrogate signal; program code for generating DRRs for each breathing phase represented by the 4D CT images; program code for generating a similarity matrix to assess a degree of resemblance in a region of interest between the DRRs and the fluoroscopic images; program code for computing a compounded similarity matrix by averaging values of the similarity matrix across different time points of the breathing phase during a breathing period of the patient; program code for determining an optimal time point synchronization between the DRRs and the fluoroscopic images by using the compounded similarity matrix; and program code for acquiring a third surrogate signal and turning a treatment beam on or off according to the optimal time point synchronization.

In an exemplary embodiment of the present invention, a computer program product comprising a computer useable medium having computer program logic recorded thereon for 4D image verification in respiratory gated radiation therapy, the computer program logic comprises: program code for acquiring 4D CT images, each of the 4D CT images representing a breathing phase of a patient and tagged with a corresponding time point of a first surrogate signal; program code for acquiring fluoroscopic images of the patient under free breathing, each of the fluoroscopic images tagged with a corresponding time point of a second surrogate signal; program code for generating DRRs for each breathing phase represented by the 4D CT images; program code for generating a similarity matrix to assess a degree of resemblance in a region of interest between the DRRs and the fluoroscopic images; program code for determining an optimal time point synchronization between the DRRs and the fluoroscopic images during a breathing period of the patient by using the similarity matrix; and program code for acquiring a third surrogate signal and turning a treatment beam on or off according to the optimal time point synchronization.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

In the following description, we will outline a four-dimensional (4D) image verification method according to an exemplary embodiment of the present invention that addresses the variability of the correlation between the amplitude of an external signal (e.g., a respiratory belt around a patient's abdominal or thoracic area or marker position placed on the patient's thorax) and the position of an internal target. The method is divided into four phases, which are described hereinafter with reference to the accompanying figures.

Planning Phase

Figure 1A:
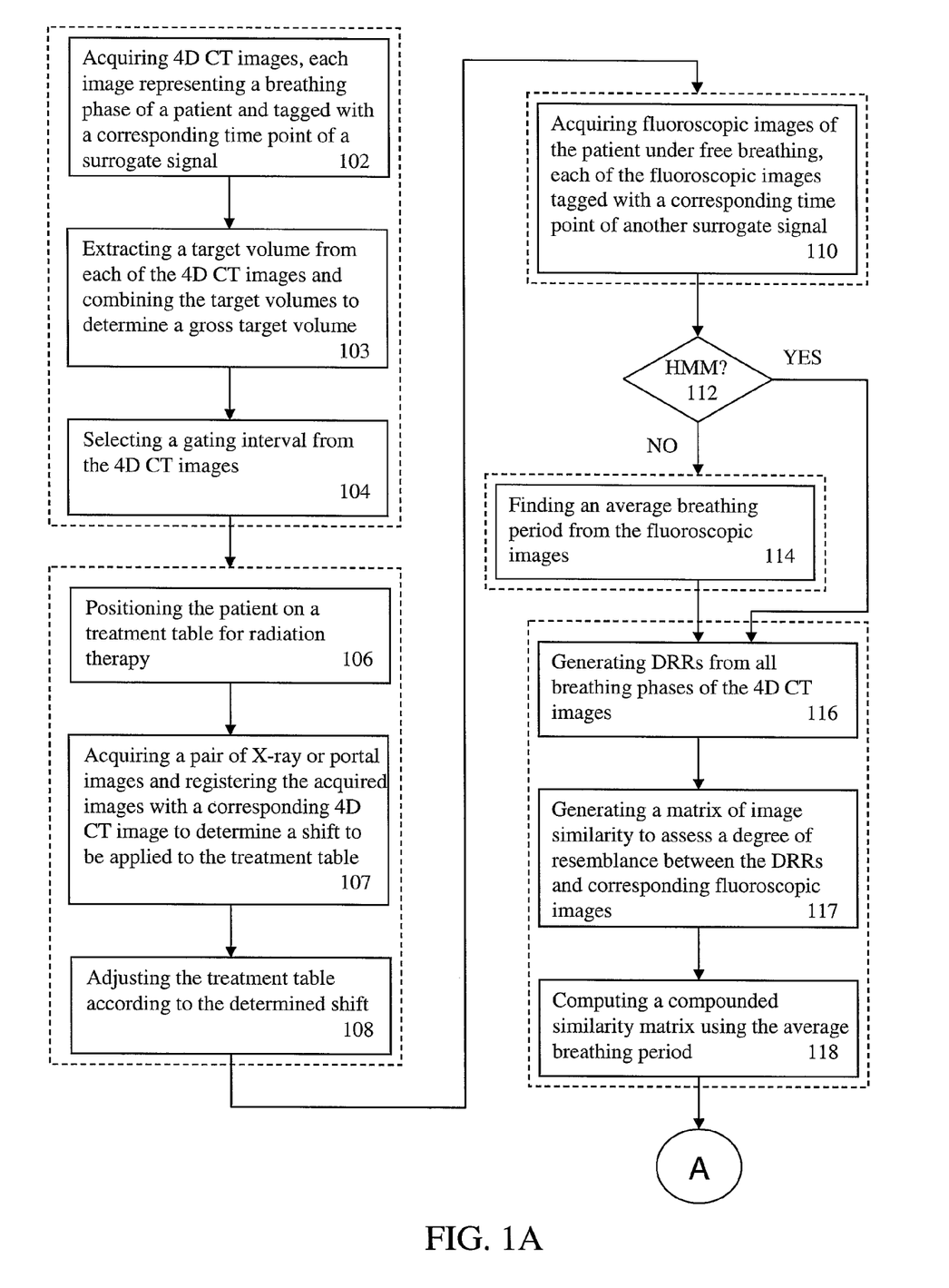
FIGS. 1A, 1B and 1C are flowcharts illustrating steps of four-dimensional (4D) image verification in respiratory gated radiation therapy according to exemplary embodiments of the present invention.

As shown in FIG. 1A, during the planning phase, a 4D computed tomography (CT) acquisition of a patient is made (102). The acquisition is made under a protocol that produces time resolved volumetric images at various phases of breathing (e.g., 8-12 phases). In other words, each image represents a breathing phase during a single breath of the patient. During this time, a surrogate signal is acquired, the surrogate signal being the acquired from, for example, a strain gauged taped on the patient's abdomen. The 4D CT scan is then processed to extract a gross target volume for the breathing phases, the gross target volume being a combined target volume from each of the breathing phases (103). Also during this phase, a gating interval that may include two or more phases (e.g., breathing phases 7-10 of a 12 phase breath) of the 4D CT is selected (104). This selection may be based on the location of the tumor, residual motion or duty cycle.

Image Guided Patient Positioning

After acquiring the 4D CT images, the initial setup is usually done by placing the patient on a treatment table and aligning laser projections with skin tattoo marks on the patient (106). An image guided method is then used to correct for residual positioning error (107). The outcome of the image guided procedure is a shift to be applied to the treatment couch. The image guided positioning in step 107 is performed on a pair of X-ray or portal images that are registered with a corresponding planning CT phase selected from the multiple time resolved phases. Here, a phase of the 4D CT that roughly corresponds to the same respiratory phase of the X-ray or portal images needs to be selected. Once the corresponding phase of the 4D CT is selected, a shift that needs to be applied to the treatment table is determined and the table is shifted accordingly (108).

Pre-Treatment Image Acquisition Phase

Patient breathing patterns can vary inter- and intra-fractionally. In this phase, we take an acquisition of a sequence of images with a corresponding surrogate signal at each time point (110). Various imaging modalities such as kilo-electron volt (KV) fluoro or mega-electron volt (MV) fluoro can be used here. In the case of MV fluoro special attention should be made as to the amount of dose delivered for the acquisition. Multiple sequences of the synchronized fluoro could also be acquired. In the case where the acquisition is not done simultaneously (e.g., using a bi-planar system), the synchronization is performed in between the acquisitions as well. For this process, the surrogate signal can be used for synchronization, following the assumption that the breathing pattern of the patient does not change in between the two acquisitions. The duration of the acquisition should be long enough to be representative of the current breathing pattern of the patient for the specific treatment session. The outcome of this phase is multiple sequences of images of the patient under free breathing condition, where each frame is tagged with a corresponding time point of the surrogate signal.

Fluoroscopic Sequence and 4D Planning Synchronization Phase

The goal of this phase is to find the relationship between the treatment image breathing pattern and the planning phase 4D CT acquisition. Since the surrogate signal is available throughout the treatment time as an indication of target motion, it is important to establish a relationship between the amplitude of the signal and actual tumor location. Once this process is done, one can infer from the signal amplitude and its variation, the probable location of the tumor.

Cycle Detection on Fluoroscopic Images

It is to be understood that this step is not performed when using the Hidden Markov Model (HMM) approach described below under the heading having the same name (112).

The first step of this process finds an "average representative" breathing period from a lengthy acquisition of the fluoroscopic images (114). This information is used for the other steps of the synchronization. We are establishing a correlation using synchronized acquisition of the fluoroscopic images. It is important to be optimal in global (e.g., average) sense rather than on cycle-by-cycle basis. The main reason is that it is well understood that the breathing pattern changes very rapidly, therefore, it is more robust to establish a correlation based on an average, which tends to change less rapidly.

To estimate the period of the breathing cycle in step 114, we first generate an auto-similarity matrix where component (i,j) is the sum of the squared differences between ith and jth images of the fluoroscopic sequence. In this matrix, we select the row with the highest cumulated dissimilarity. This gives us a one-dimensional (1D) periodic signal from which the period of the cycle can be detected.

The signal is processed to determine the best fitting Autoregressive (AR) model. This AR model is used in turn to compute the signal frequency. Given a first order AR model $X[t]=A.X[t-1]$, the signal frequency is the complex argument of the largest eigenvalue of A.

Synchronization Fluoro/DRR

The first step here is to generate digitally reconstructed radiographs (DRRs) from all the phases of the 4D CT at the treatment position (116). These DRRs are supposed to be aligned rigidly with the fluoroscopic images. The remaining discrepancy is an unmatched breathing phase. The second step is to generate a matrix of image similarity, which accesses the degree of resemblance in a particular region of interest between planning time varying DRRs and fluoroscopic images (117).

The similarity metric used here could be one or a combination of the flowing: mutual information, correlation ratio, gradient correlation, gradient difference, normalized cross correlation, local normalized cross correlation, etc.

The region of interest on which the similarity is computed can be either manually specified by the user or estimated from the projected position of the gross target volume on both time-varying DRRs and fluoroscopic images.

The third step is to compute the compounded similarity matrix using the average period from the cycle detection phase (118). The compounding involves averaging the value of the similarity metric across different time points of the breathing cycles using the average period detected from the images. The compounding approach helps increase the signal to noise ratio of the computed similarity metric. Once the similarity matrix is estimated, several approaches can be applied to obtain the correspondences DRR/Fluoro (120). If the following, we describe three possibilities.

Image Similarity and Shortest Path

Figure 1B:
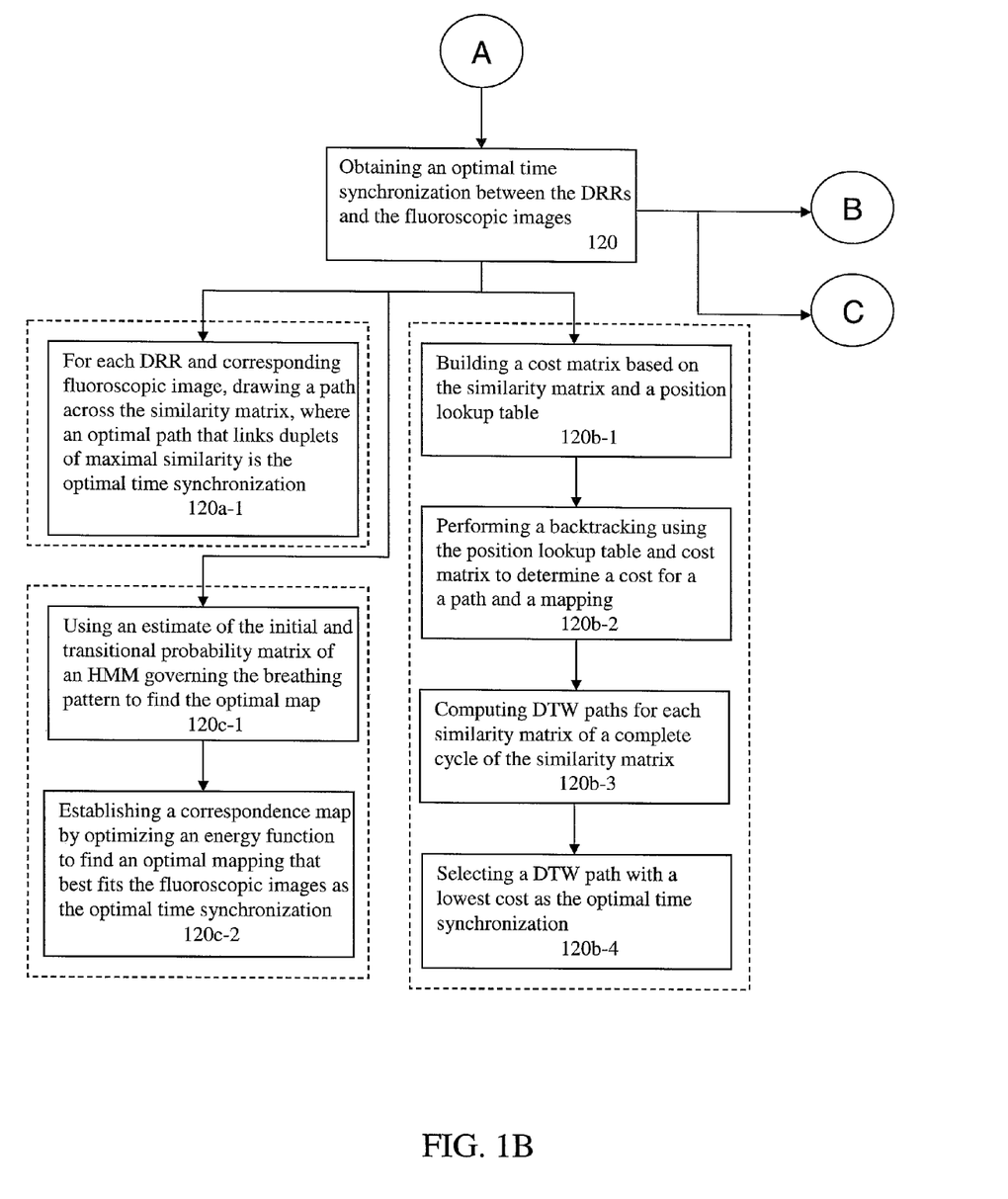

Referring now to FIG. 1B, the similarity matrix is used to determine the optimal time synchronization between the DRRs and fluoroscopic images. Here, when each DRR is associated to a fluoroscopic image, a path is drawn across the similarity matrix, and the optimal path is the one that links the duplets (DRR, fluoro) of maximal similarity (120a-1). Therefore, determining the optimal time association is equivalent to finding the path of maximal cost (e.g., maximal sum or similarities) across the similarity matrix.

Image Similarity and Dynamic Time Warping

The Dynamic Time Warping (DTW) approach is similar to the shortest path approach described in the Image Similarity and Shortest Path section. Derived from speech recognition, where the algorithm is used to treat signals with different speaking speeds, we can use the algorithm to find a mapping between the two signals (DRRs and fluoroscopic images). Once the similarity matrix, as described above, is generated, the algorithm can be applied. DTW and the Dijkstra algorithm are both based on Dynamic Programming (DP). The basic principle of DP is based on the proposition that any subset of any optimal solution is also optimal (Bellman principle of optimality).

In the first step, a cost-matrix is built upon the similarity matrix (120b-1). Therefore, the matrix is extended as shown below in Table 1.

TABLE 1

| 0 | InF | InF | InF | InF |
|---|---|---|---|---|
| InF | | | | |
| InF | | Sim matrix | | |
| InF | | | | |

In this table, InF depicts a high cost. Starting from the top left index, the costs are computed the following way. The minimum value out of the three positions next to the actual cell will be added toe the value (e.g., 0+min (InF,InF,0.8)), as shown below in Table 2.

TABLE 2

| 0 | | |
|---|---|---|
| | InF | ... |
| InF | 0.8 | ... |
| ... | ... | ... |

Within this step a lookup table is built up, containing the position of the minimal values added to the actual (left|right|diagonal). Once this step is complete, the second step can be processed (120b-2). The second step does backtracking, starting from the bottom right of the matrix. Using the position lookup table and the cost matrix, a backtracking is performed. The result is an overall cost for the path and a mapping as shown below in Table 3.

TABLE 3

| 1 | 2 | 2 |
|---|---|---|
| 2 | 1 | 2 |
| 2 | 1 | 2 |

We also implemented a cycling of the similarity matrix, here the DTW paths for each similarity matrix of one complete cycle is computed (120b-3). The DTW path with the lowest costs will be selected (120b-4).

Hidden Markov Modeling Approach

An HMM is described by a set of discrete states, transitional probability and initial state probability. Given a set of instances of state sequences, one can learn the HMM parameters, and consequently generate more instances of the same process.

One way to establish the model between the tumor position and fluoroscopic image sequence is to take advantage of HMMs. We can assume that the breathing cycle could be segmented into different states. We consider all the phases of the planning 4D CT and one irregular state accounting for possible derivation from the motion/state observed doing 4D CT acquisition. The states (e.g., locations of tumor volume) are hidden and only observed through the fluoroscopic images, e.g., linked via DRRs, and the belt signal amplitude. During the modeling phase, the initial and transition probability matrix of the HMM should be estimated (120c-1). For simplicity, we could also consider uniform initial probability, and handcraft a transition probability matrix based on predefined rules regarding the human breathing pattern. It is important to note that we assume the number of states is fixed in this case.

To establish a correspondence map, we optimize an energy function that consists of two terms. The first term evaluates the cost of the similarity using the computed similarity matrix. The second term evaluates the likelihood of the hypothesized sequence based on the learned HMM. By minimizing this two term energy function, we find the optimal mapping, which best fits the images and is consistent with the breathing pattern (120c-2).

Learning the Variation of the Surrogate Signal

Figure 1C:
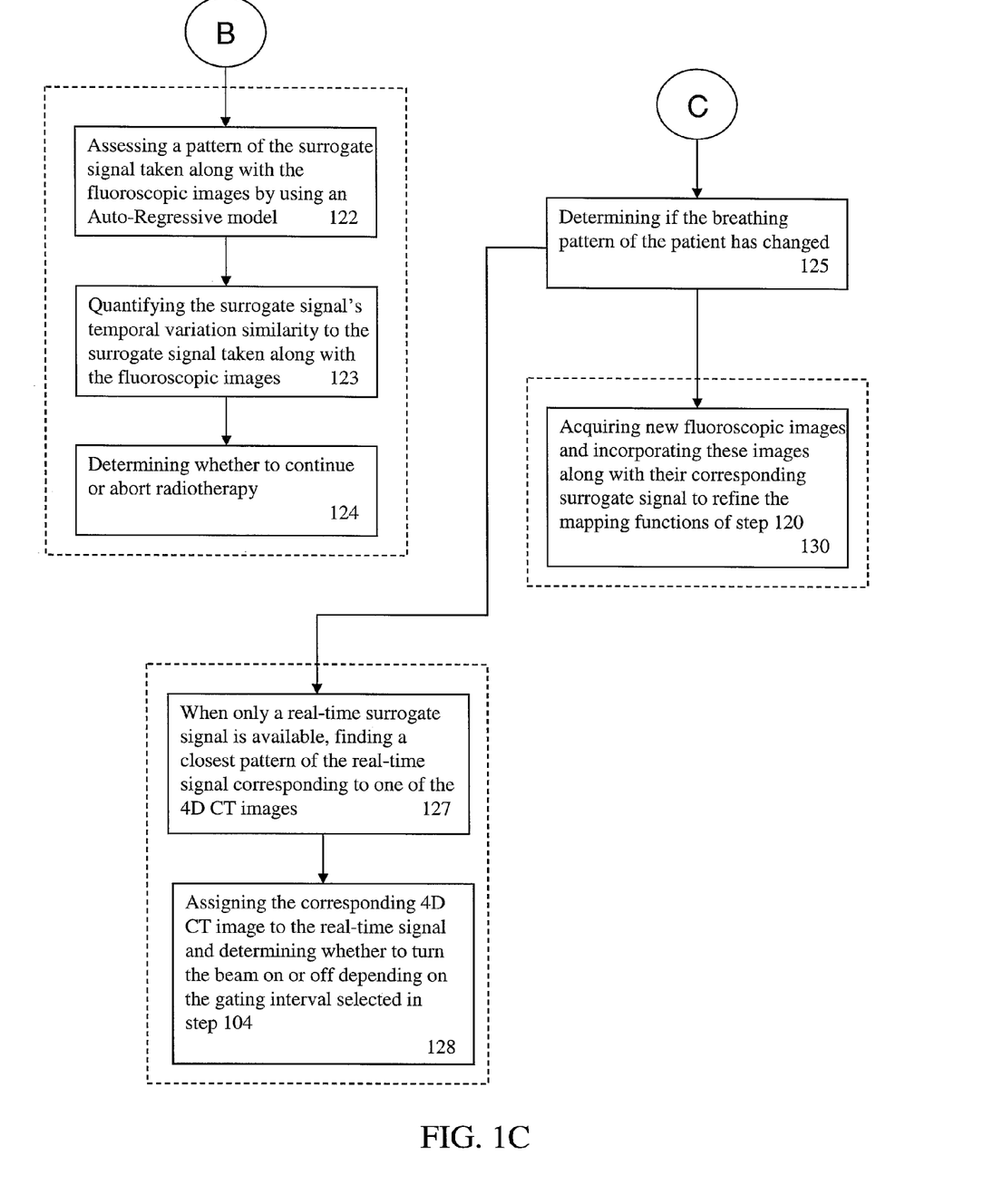

Referring now to FIG. 1C, another important aspect of the image verification for 4D treatment is analysis of the surrogate signal. In gated radiotherapy, the surrogate signal which is available in real-time can be used to infer target location, having done the preliminary image guided verification shortly before treatment. However, a check needs to be done to quantify whether the surrogate signal pattern has remained relatively consistent from the pre-treatment verification to the actual treatment phase.

For this purpose, we use Auto-Regressive (AR) models to assess the pattern of the surrogate signal taken along with the fluoroscopic sequence for image verification process (122). An AR model consists of the set of coefficients that can be used to estimate/predict the amplitude of the surrogate signal at the given time via linear combination of the signal's amplitude history (samples at previous time steps). The AR coefficients can be estimated from a given signal via a list squares method. The number of coefficients is related to residual error of the modeling procedure. We set a tolerance on the residual error (e.g., 5% of the maximum signal amplitude) and estimate a set of AP parameters, which can provide below the tolerance modeling residual error. Given a new signal, we can quantify its temporal variation similarity to the reference signal (123) and make a decision whether to continue or abort the treatment (124).

4D Treatment

We can consider two modes of operation during the treatment, when the radiation beam is on. During the first mode, only a real-time surrogate signal is available. Therefore, the breathing stage/phase has to be inferred from the breathing signal alone. In the second mode, a sporadic acquisition of the x-ray images of the treatment site is also available along with the surrogate signal. In this mode, an additional level of adaptation could be performed based on newly acquired X-ray images. Before doing any operation, we first need to make sure that the breathing signal pattern is not changed (125). This is done through measuring the residual error based on the leaned AR model as described in the Learning the Variation of the Surrogate Signal section. Here we put a threshold on the residual error to make sure we remain within the acceptable range that is set during the modeling phase. If the residual error is within the acceptable range, the new fluoroscopic image is incorporated.

Inferring Respiratory Stage from the Surrogate Signal

In this stage, the synchronization results as described in the Fluoroscopic Sequence and 4D Planning and Synchronization Phase section are utilized. Synchronization methods of the Synchronization Fluoro/DRR section provide a mapping function that relates the amplitude of the surrogate signal (along with some temporal variation through history) to the respiratory phase observed during the 4D CT acquisition. To utilize this information given a surrogate signal during the treatment time, we first search and find the closest pattern of the surrogate corresponding to the 4D CT respiratory phase (127). Second, we assign the corresponding 4D CT respiratory phase to that instance of the surrogate signal amplitude and determine whether to turn the beam on or off depending on the gating interval selected in step 104 (128). Temporal consistency could also be enforced by making the search order dependent.

Adaptation During Treatment

In cases where sporadic acquisition of X-ray images are performed, one can incorporate these images along with the corresponding belt signal amplitude to refine the mapping function for the approaches described in the Synchronization Fluoro/DRR section (130). This level of the adaptation could only be done if the breathing signal characteristic has remained consistent as compared to the learned AR model. The only changes, which can be accounted for here are the appearance and position change of the target volume in the new acquisitions.

Exemplary embodiments of the present invention are provided to find the correlation between the external signal amplitude (e.g., marker position) and the internal target position (e.g., tumor) for image verification in respiratory gated radiation therapy. The main issue in performing this task is to robustly find a mapping between a set of fluoroscopic images and phases of 4D CT compared via DRR images. Once the link between the image sequences is established, one can relate the surrogate signal to the planning breathing phases at treatment time. We also learn the temporal variation of the breathing surrogate signal and check for the consistency of the pattern during the treatment phase.

Systems in which exemplary embodiments of the present invention may be implemented will now be described.

Figure 2:
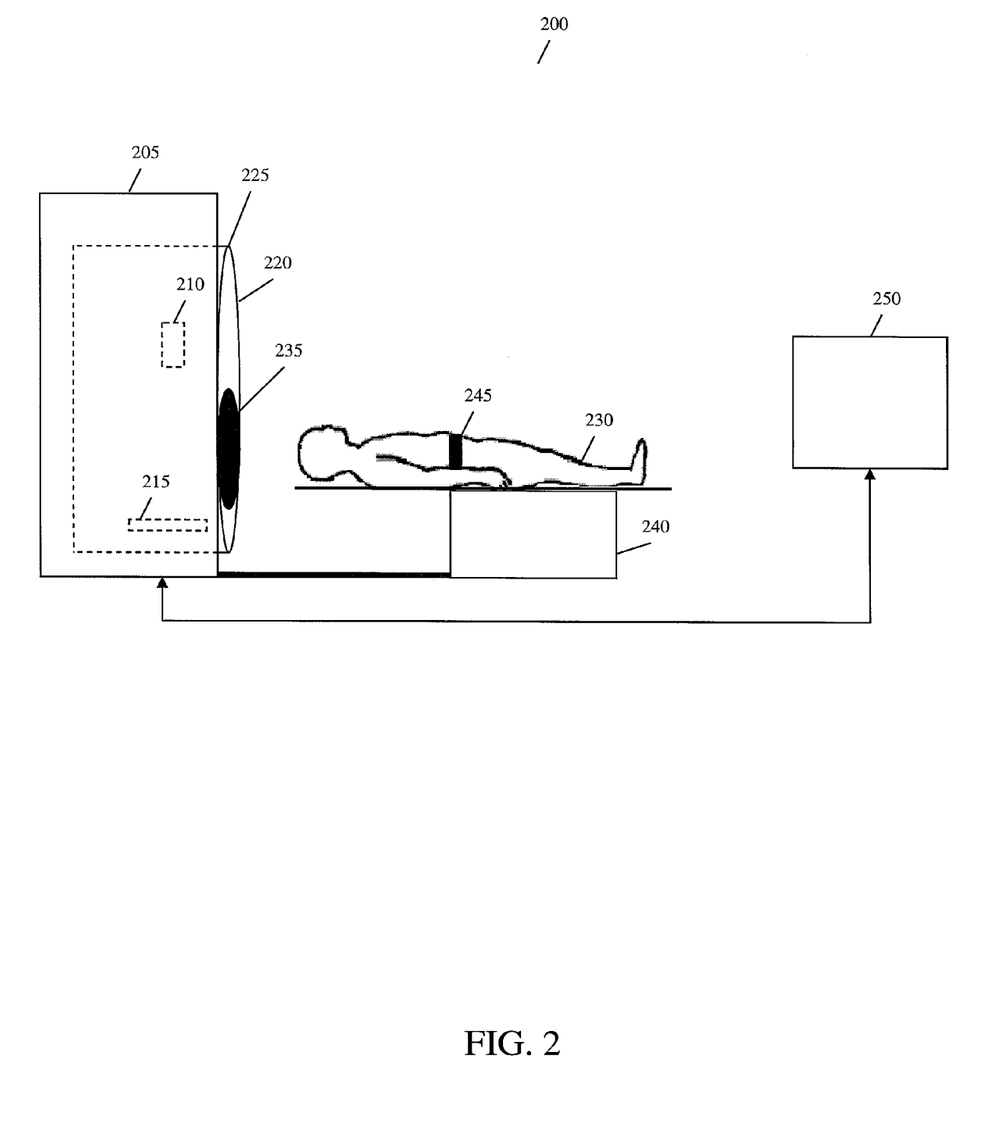
FIG. 2 is a block diagram illustrating a computed tomography (CT) system in which exemplary embodiments of the present invention may be implemented.

FIG. 2 is a block diagram illustrating a CT system 200 that includes a CT base 205, a source of imaging energy 210, a detector array 215, an annular rotating gantry 220 having an outer circumference 225, and an electronics system 250 such as a computer to obtain multiple X-ray images of patient 230 and signals associated with a respiratory monitor 245 secured to a portion of the patient's 230 chest.

The detector array 215 includes a plurality of detectors, for example, several thousand detectors, which generate X-ray data that is utilized to simultaneously construct multiple image slices. The detector array 215 is typically mechanically coupled to the gantry 220 and rotates therewithin. In an exemplary embodiment, the gantry 220 is about four feet in diameter and rotates at about two revolutions per second.

The patient 230 is generally positioned near a central aperture 235 of the gantry 220 on a table 240 that is axially movable along the base 205, enabling respective X-ray slices to be obtained at multiple axial positions. The X-ray slices are processed at the electronics system 250 to produce enhanced images for diagnoses or inspection.

Figure 3:
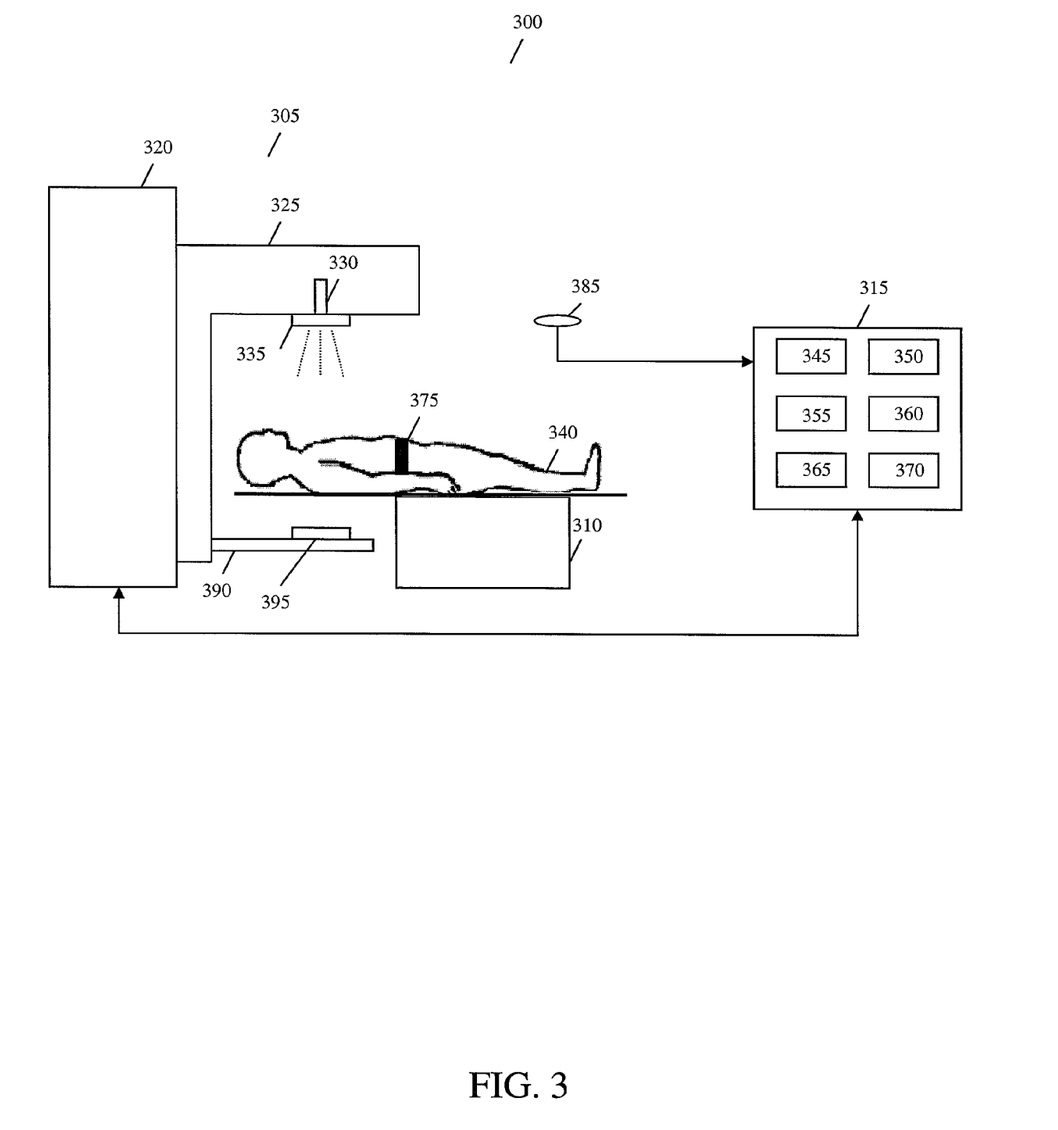
FIG. 3 is a block diagram illustrating a linear accelerator (LINAC) system in which exemplary embodiments of the present invention may be implemented.

FIG. 3 is a block diagram illustrating a linear accelerator (LINAC) system 300 that includes a LINAC device 305, a bed 310 and a treatment unit 315. The LINAC device 305 includes, inter alia, a base 320, which includes a control unit for controlling the LINAC device 305, and a gantry 325. The gantry 325 includes a LINAC 330 or an X-ray KV imaging source, a beam-shielding device (not shown) within a treatment head 335, and a KV or MV imaging panel 395 attached to an electronic portal imaging device 390.

The gantry 325 can be swiveled about a horizontal axis during the course of radiation treatment or radiotherapy. The treatment head 335 is fixed to the gantry 325 for movement therewith, and the LINAC 330 or X-ray KV imaging source generates high-powered radiation such as electron, photon or any other detectable radiation. The movement of the gantry 325 and distribution of radiation from the LINAC 330 are controlled by the control unit in response to commands issued from the treatment unit 315.

As shown in FIG. 3, the electronic portal imaging device 390 is mounted to the gantry 325. Portal images can be obtained at any gantry 325 angle and during rotation of the gantry 325. The portal imaging device 390 includes the imaging panel 395, which may be a flat panel amorphous silicon detector implemented as one or more arrays of photo-sensors. The panel 395 is capable of measuring the radiation exiting the patient 340. The amount of radiation exiting the patient 340 can be used to gather the patient's 340 exit dose information. The delivered radiation dose can then be compared to a planned delivery dose using DRRs generated by the treatment unit 315 to determine if the delivered radiation dose went as planned.

The treatment unit 315 includes, inter alia, a central processing unit (CPU) 345 and a memory 350, both of which may be connected to an input device 355 and output device 360. The treatment unit 315 includes a module 365 that includes one or more methods for 4D image verification in respiratory gated radiation therapy according to exemplary embodiments of the present invention. The treatment unit 315 also includes a module 370 that includes patient treatment information based on previously acquired CT data. The memory 350 may include a random access memory (RAM) and a read only memory (ROM). The memory 350 may also include a database, disk drive, tape drive, or a combination thereof for storing patient treatment information. The input 355 may be constituted by a keyboard or mouse and the output 360 may be constituted by a liquid crystal display (LCD) or cathode ray tube (CRT) display.

As further shown in FIG. 3, a patient 340 includes a respiratory monitor 375 in the form of a belt secured to a portion of his chest. The respiratory monitor 375 may be, for example, a respiratory monitoring belt such as a strain gauge that generates a signal in synch with the breathing motion of the patient's 340 chest. The signal may be transmitted to the treatment unit 315 via a sensor 385 or directly via a hardwired connection. The respiratory monitor 375 may also be an optical marker attached to the patient's chest or abdomen that works in conjunction with the sensor 385, which in this example is an optical sensor, to transmit data associated with the respiratory state of the patient 340 to the treatment unit 315.

It should be understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It should also be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It is further understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for four-dimensional (4D) image verification in respiratory gated radiation therapy, comprising:

acquiring 4D computed tomography (CT) images, each of the 4D CT images representing a breathing phase of a patient and tagged with a corresponding time point of a first surrogate signal;

acquiring fluoroscopic images of the patient under free breathing, each of the fluoroscopic images tagged with a corresponding time point of a second surrogate signal;

generating digitally reconstructed radiographs (DRRs) for each breathing phase represented by the 4D CT images;

generating a similarity matrix to assess a degree of resemblance in a region of interest between the DRRs and the fluoroscopic images;

computing a compounded similarity matrix by averaging values of the similarity matrix across different time points of the breathing phase during a breathing period of the patient;

determining an optimal time point synchronization between the DRRs and the fluoroscopic images by using the compounded similarity matrix; and acquiring a third surrogate signal and turning a treatment beam on or off according to the optimal time point synchronization.

2. The method of claim 1, wherein determining an optimal time point synchronization between the DRRs and the fluoroscopic images comprises:

drawing a path across the compounded similarity matrix for each DRR that is associated to a fluoroscopic image, wherein a path that links duplets of maximal similarity represents the optimal time point synchronization.

3. The method of claim 1, wherein determining an optimal time point synchronization between the DRRs and the fluoroscopic images comprises:

building a cost matrix upon the compounded similarity matrix;

building a position lookup table that contains values in the cost matrix;

performing a backtracking using the position lookup table and the cost matrix to determine costs for paths in the cost matrix; and selecting a path with a lowest cost that represents the optimal time point synchronization.

4. The method of claim 1, wherein determining an optimal time point synchronization between the DRRs and the fluoroscopic images comprises:

establishing a correspondence map between the DRRs and the fluoroscopic images; and minimizing an energy function to find an optimal mapping between the DRRs and the fluoroscopic images, the optimal mapping representing the optimal time point synchronization.

5. The method of claim 4, wherein the energy function is a two term energy function, the first term evaluating a cost of similarity between the DRRs and the fluoroscopic images on the correspondence map and the second term evaluating a likelihood of a hypothesized fluoroscopic image sequence based on a learned Hidden Markov Model (HMM).

6. The method of claim 1, further comprising:
determining a consistency between the time points of the second surrogate signal and the time points of the third surrogate signal by using an Auto-Regressive (AR) model built according to the second surrogate signal.

7. The method of claim 1, wherein the breathing period of the patient is an average breathing period that is determined by:
generating an auto-similarity matrix and from this matrix selecting a row with a highest cumulated dissimilarity to generate a one-dimensional (1D) periodic signal;
processing the 1D periodic signal to determine a best fitting AR model, the AR model built according to the second surrogate signal; and
computing the average breathing period using the best fitting AR model.

8. The method of claim 1, wherein the similarity matrix generated to assess a degree of resemblance in a region of interest between the DRRs and the fluoroscopic images is one or a combination of mutual information, correlation ratio, gradient correlation, gradient difference, normalized cross correlation or local normalized cross correlation.

9. The method of claim 1, wherein after acquiring the 4D CT images and before acquiring the fluoroscopic images the method further comprises:
extracting a target volume from each of the 4D CT images and combining the target volumes to determine a gross target volume.

10. The method of claim 9, wherein the region of interest is manually specified by a user or estimated from a position of the gross target volume on the DRRs and the fluoroscopic images.

11. The method of claim 1, wherein the first, second and third surrogate signals correspond to a target inside the patient.

12. The method of claim 11, wherein the target is a tumor location or a suspected location of a tumor.

13. A method for four-dimensional (4D) image verification in respiratory gated radiation therapy, comprising:
acquiring 4D computed tomography (CT) images, each of the 4D CT images representing a breathing phase of a patient and tagged with a corresponding time point of a first surrogate signal;
acquiring fluoroscopic images of the patient under free breathing, each of the fluoroscopic images tagged with a corresponding time point of a second surrogate signal;
generating digitally reconstructed radiographs (DRRs) for each breathing phase represented by the 4D CT images;
generating a similarity matrix to assess a degree of resemblance in a region of interest between the DRRs and the fluoroscopic images;
determining an optimal time point synchronization between the DRRs and the fluoroscopic images during a breathing period of the patient by using the similarity matrix; and
acquiring a third surrogate signal and turning a treatment beam on or off according to the optimal time point synchronization.

14. The method of claim 13, wherein determining an optimal time point synchronization between the DRRs and the fluoroscopic images comprises:
drawing a path across the similarity matrix for each DRR that is associated to a fluoroscopic image, wherein a path that links duplets of maximal similarity represents the optimal time point synchronization.

15. The method of claim 13, wherein determining an optimal time point synchronization between the DRRs and the fluoroscopic images comprises:
building a cost matrix upon the similarity matrix;
building a position lookup table that contains values in the cost matrix;
performing a backtracking using the position lookup table and the cost matrix to determine costs for paths in the cost matrix; and
selecting a path with a lowest cost that represents the optimal time point synchronization.

16. The method of claim 13, wherein determining an optimal time point synchronization between the DRRs and the fluoroscopic images comprises:
establishing a correspondence map between the DRRs and the fluoroscopic images; and
minimizing an energy function to find an optimal mapping between the DRRs and the fluoroscopic images, the optimal mapping representing the optimal time point synchronization.

17. The method of claim 16, wherein the energy function is a two term energy function, the first term evaluating a cost of similarity between the DRRs and the fluoroscopic images on the correspondence map and the second term evaluating a likelihood of a hypothesized fluoroscopic image sequence based on a learned Hidden Markov Model (HMM).

18. The method of claim 13, further comprising:
determining a consistency between the time points of the second surrogate signal and the time points of the third surrogate signal by using an Auto-Regressive (AR) model built according to the second surrogate signal.

19. The method of claim 13, wherein the breathing period of the patient is an average breathing period that is determined by:
generating an auto-similarity matrix and from this matrix selecting a row with a highest cumulated dissimilarity to generate a one-dimensional (1D) periodic signal;
processing the 1D periodic signal to determine a best fitting AR model, the AR model built according to the second surrogate signal; and
computing the average breathing period using the best fitting AR model.

20. The method of claim 13, wherein the similarity matrix generated to assess a degree of resemblance in a region of interest between the DRRs and the fluoroscopic images is one of a combination of mutual information, correlation ratio, gradient correlation, gradient difference, normalized cross correlation or local normalized cross correlation.

21. The method of claim 13, wherein after acquiring the 4D CT images and before acquiring the fluoroscopic images the method further comprises:
extracting a target volume from each of the 4D CT images and combining the target volumes to determine a gross target volume.

22. The method of claim 21, wherein the region of interest is manually specified by a user or estimated from a position of the gross target volume on the DRRs and the fluoroscopic images.

23. The method of claim 13, wherein the first, second and third surrogate signals correspond to a target inside the patient.

24. The method of claim 23, wherein the target is a tumor location or a suspected location of a tumor.

25. A system for four-dimensional (4D) image verification in respiratory gated radiation therapy, comprising:
- a memory device for storing a program;
- a processor in communication with the memory device, the processor operative with the program to:
  - acquire 4D computed tomography (CT) images, each of the 4D CT images representing a breathing phase of a patient and tagged with a corresponding time point of a first surrogate signal;
  - acquire fluoroscopic images of the patient under free breathing, each of the fluoroscopic images tagged with a corresponding time point of a second surrogate signal;
  - generate digitally reconstructed radiographs (DRRs) for each breathing phase represented by the 4D CT images;
  - generate a similarity matrix to assess a degree of resemblance in a region of interest between the DRRs and the fluoroscopic images;
  - compute a compounded similarity matrix by averaging values of the similarity matrix across different time points of the breathing phase during a breathing period of the patient;
  - determine an optimal time point synchronization between the DRRs and the fluoroscopic images by using the compounded similarity matrix; and
  - acquire a third surrogate signal and turn a treatment beam on or off according to the optimal time point synchronization.

26. A system for four-dimensional (4D) image verification in respiratory gated radiation therapy, comprising:
- a memory device for storing a program;
- a processor in communication with the memory device, the processor operative with the program to:
  - acquire 4D computed tomography (CT) images, each of the 4D CT images representing a breathing phase of a patient and tagged with a corresponding time point of a first surrogate signal;
  - acquire fluoroscopic images of the patient under free breathing, each of the fluoroscopic images tagged with a corresponding time point of a second surrogate signal;
  - generate digitally reconstructed radiographs (DRRs) for each breathing phase represented by the 4D CT images;
  - generate a similarity matrix to assess a degree of resemblance in a region of interest between the DRRs and the fluoroscopic images;
  - determine an optimal time point synchronization between the DRRs and the fluoroscopic images during a breathing period of the patient by using the similarity matrix; and
  - acquire a third surrogate signal and turn a treatment beam on or off according to the optimal time point synchronization.

27. A computer program product comprising a computer useable medium having computer program logic recorded thereon for four-dimensional (4D) image verification in respiratory gated radiation therapy, the computer program logic comprising:
- program code for acquiring 4D computed tomography (CT) images, each of the 4D CT images representing a breathing phase of a patient and tagged with a corresponding time point of a first surrogate signal;
- program code for acquiring fluoroscopic images of the patient under free breathing, each of the fluoroscopic images tagged with a corresponding time point of a second surrogate signal;
- program code for generating digitally reconstructed radiographs (DRRs) for each breathing phase represented by the 4D CT images;
- program code for generating a similarity matrix to assess a degree of resemblance in a region of interest between the DRRs and the fluoroscopic images;
- program code for computing a compounded similarity matrix by averaging values of the similarity matrix across different time points of the breathing phase during a breathing period of the patient;
- program code for determining an optimal time point synchronization between the DRRs and the fluoroscopic images by using the compounded similarity matrix; and
- program code for acquiring a third surrogate signal and turning a treatment beam on or off according to the optimal time point synchronization.

28. A computer program product comprising a computer useable medium having computer program logic recorded thereon for four-dimensional (4D) image verification in respiratory gated radiation therapy, the computer program logic comprising:
- program code for acquiring 4D computed tomography (CT) images, each of the 4D CT images representing a breathing phase of a patient and tagged with a corresponding time point of a first surrogate signal;
- program code for acquiring fluoroscopic images of the patient under free breathing, each of the fluoroscopic images tagged with a corresponding time point of a second surrogate signal;
- program code for generating digitally reconstructed radiographs (DRRs) for each breathing phase represented by the 4D CT images;
- program code for generating a similarity matrix to assess a degree of resemblance in a region of interest between the DRRs and the fluoroscopic images;
- program code for determining an optimal time point synchronization between the DRRs and the fluoroscopic images during a breathing period of the patient by using the similarity matrix; and
- program code for acquiring a third surrogate signal and turning a treatment beam on or off according to the optimal time point synchronization.

\* \* \* \* \*